United States Patent [19]

Mitchell, Sr. et al.

[11] 4,182,238
[45] Jan. 8, 1980

[54] SELF CONTAINED PRESSURE VESSEL

[76] Inventors: John W. Mitchell, Sr., 1701 W. 168th St.; Kenneth H. Oyama, 1601 W. Redondo Beach Blvd., both of Gardena, Calif. 90247; John K. Lawler, deceased, late of Gardena, Calif.; by Doris G. Lawler, executrix, 16616 Taylor Ct., Gardena, Calif. 90247

[21] Appl. No.: 871,476

[22] Filed: Jan. 23, 1978

[51] Int. Cl.² ............................................. B30B 15/00
[52] U.S. Cl. ................................ 100/99; 100/269 R; 100/289; 264/17; 425/170; 425/177
[58] Field of Search ..................... 100/99, 289, 269 R; 425/170, 446, 177, 178, 180; 72/63; 264/17, 84

[56] References Cited
U.S. PATENT DOCUMENTS

| | | | |
|---|---|---|---|
| 2,864,125 | 12/1958 | Kelley | 100/99 X |
| 2,887,946 | 5/1959 | Barnes et al. | 100/99 |
| 3,450,039 | 6/1969 | Ashbrook | 100/269 R |

Primary Examiner—Billy J. Wilhite
Attorney, Agent, or Firm—Howard L. Johnson

[57] ABSTRACT

A transparent, generally cylindrical, wide-mouth pressure retaining vessel or container cast of synthetic resin with a surrounding side wall formed by successively downwardly inset, annular wall segments, and externally reinforced by integral vertical ribs with successive annular edges of the inner stepped face providing support ledges adapted to hold removable shelves upon which freshly cast dentures, acrylic hobby items, pressure-curable art objects, etc. as well as fermentable foodstuff and gas-generating chemicals may be placed for exposure to externally applied and/or internally generated fluid pressure (gas or liquid). Necessity for retention clamps is eliminated by a threadedly mounted closure which carries a manually operable, threaded piston stem disposing a piston in an open-bottom chamber of the cover, which chamber projecting into a container full of liquid causes the latter to fill the piston chamber upon the cover being mounted on the container. This forms a hydraulic ram for application of pressure to objects immersed in the contained fluid. Air supplied under pressure through an inlet valve may be substituted in whole or part for liquid. The cover is reinforced by external spoke-like ribs and is recessed to form a catch basin to retain liquid spill from piston chamber bleed lines upon initial mounting of the cover.

5 Claims, 6 Drawing Figures

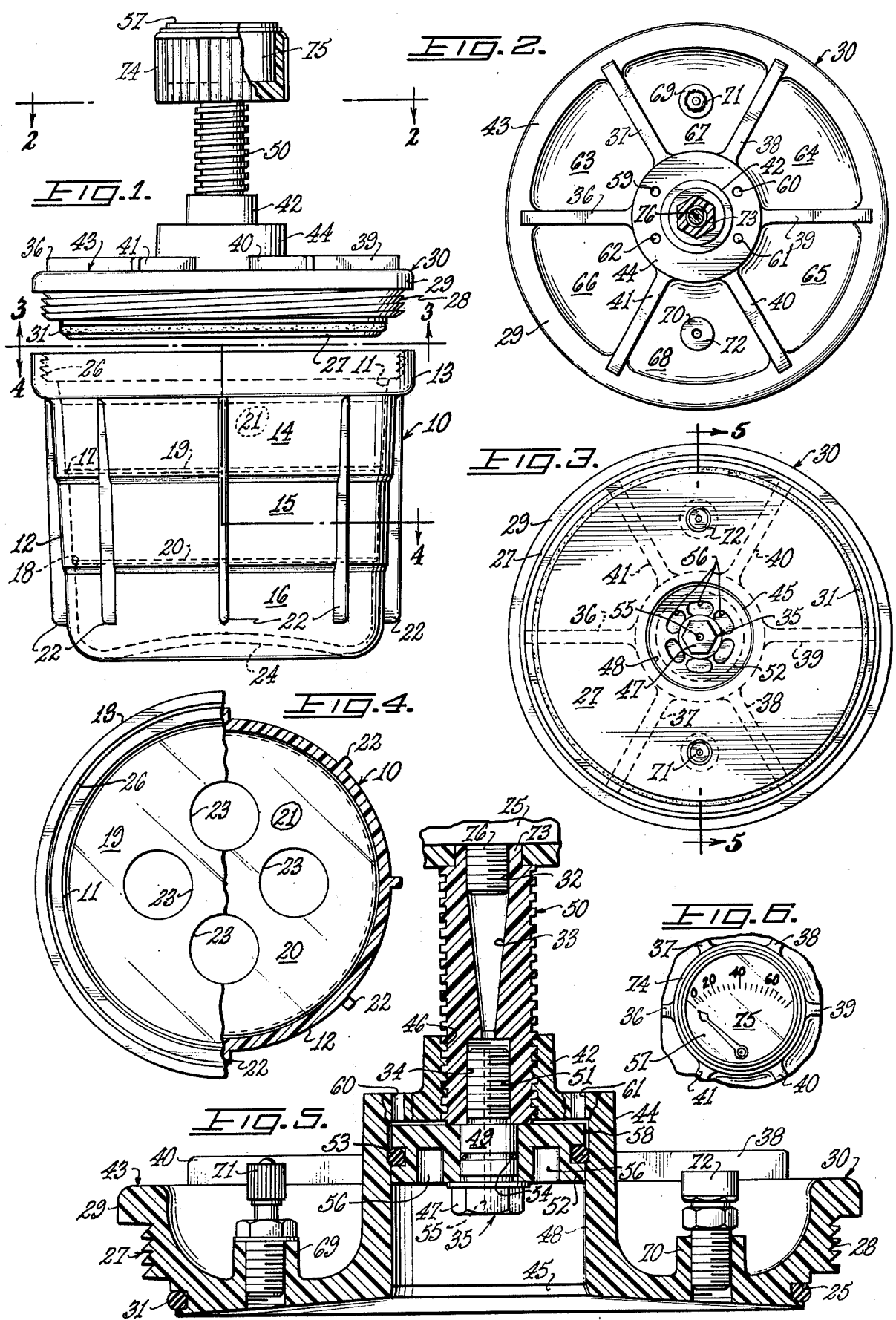

SELF CONTAINED PRESSURE VESSEL

BACKGROUND OF THE INVENTION

Large dental laboratories have heavy, reinforced pressure vessels, like cookers, which will apply a high fluid pressure to a considerable quantity of various objects, often with simultaneous application of heat. However it would be desirable to have a small, portable, self-contained, inexpensive pressure unit in which either a lone technician or dentist can quickly cure, say, a single pair of dentures or a molded trinket without leaving the office or workbench, or alternately can carry such unit on a field trip and there cure dentures or other articles with either gas or liquid pressure and in the absence of associated equipment such as an air compressor or thermal elements. Thus if such pressure vessel were available, a small plastic object could be "cold cured" at a minimum of say 18 to 20 PSI for a limited curing cycle which would prevent retention of gas bubbles or voids which might otherwise result from reaction with catalytic material found intimately mixed with the setting plastic or resin.

However the fragile nature of the general class of synthetic resins has prevented their use in forming such a high pressure reaction chamber as a small unit. Alternately, use of the more expensive metals, such as steel, is generally limited to larger and more costly assemblies. By way of comparison with the present unit, a resilient plastic vessel limited to use of hydraulic pressure and requiring metallic closure clamps is shown in U.S. Pat. No. 3,450,039.

STATEMENT OF THE INVENTION

It has now been found that with the use of the present reinforced wall structure and arrangement of parts, a small, portable, unitary assembly can be produced of transparent, synthetic resin (typically polycarbonate such as "Lexan" or "Merlon" TM) which will readily carry a test pressure of 200 PSI or more and hence can very safely bear a self-generated (i.e. manually effected) internal operating pressure of either gas and/or liquid on the order of 30 PSI or higher, and additionally will not require clamps for closure. It can be operated by an amateur simply by filling the container with water, tightening the cover thereon, and manually turning the piston stem to axially depress the piston, first to close a bleed line and then to act as a hydraulic ram on the body of contained liquid and exert a corresponding pressure on the objects immersed in the fluid. A pressure relief valve may be set for 28 or 30 PSI. Additionally, an air inlet valve on the cover allows introduction of pressurized gas (air), either to augment an incomplete volume of liquid or in some instances to substitute for it. Thus connection may be made to an air compressor, if available, or recourse may simply be to a hand pump such as used to inflate bicycle or automobile tires. In such case, a little water is also added to insure a humid atmosphere for curing. If heat is desired for the particular material being cured, hot water can be added to the container, to heat the whole assembly.

In addition to curing molded plastics, the pressure vessel has been found useful as a reaction-container to retain or transport fermenting foodstuff such as sauerkraut, marinating fish, pickles, etc. as well as to confine gas-evolving chemicals including carbonating liquids.

Structurally, there is injection molded of polycarbonate resin (such as "Lexan" produced by General Electric Co. or "Merlon" by Mobay Chem. Co.) a wide-mouth, open-top, generally cylindrical container wherein encircling side walls are formed by a pattern providing a vertical series of generally annular segments or bands, successively downward inset from a mouth-encircling segment, with their respective inner projecting edges forming separate ledges for removable shelves and their external face formed integral with a peripherally spaced series of vertical reinforcing ribs extending radially outward to a peripheral extent generally equal to that of the mouth-embracing segment. A similarly cast cover or closure is formed of lubricious grade plastic, i.e. General Electric Co. phenylene base resin known as "Noryl 737". A threaded lip is disposed to engage the correspondingly threaded mouth. Centrally, the underface of the cover is formed with a bottom-open piston chamber which (upon the cover being mounted on the container when it is filled with liquid) projects into and is filled by the liquid as the cover is screwed down. Excess liquid runs out bleed lines at the top of the chamber, which are open only while the piston is in its uppermost or retracted position.

The piston chamber originates in a central or axial turret upstanding from the top of the cover and threadedly traversed by a piston stem having rectangular threads. The piston rod or stem is tubular and proximately carries an operating knob in which a pressure gage is embedded which is in fluid communication with the interior of the container by the tubular piston stem and a lengthwise aperture of a coupling bolt which fastens the piston to the stem. The cover also carries an air inlet valve and a pressure relief valve and is formed with radially extending ribs or spokes, between which it is recessed to form a collective splash basin which catches the liquid forced out through the bleed lines. This prevents such overflow from running down the sides and wetting the technician's workbench.

BRIEF DESCRIPTION OF THE DRAWINGS

FIG. 1 is an elevational view of the Pressure Vessel with the cover shown separated from the container and a portion of the operating knob broken away to show the pressure gage therein.

FIG. 2 is a transverse section taken through the piston stem along the line 2—2 of FIG. 1, the top of the cover appearing in plan view.

FIG. 3 is a bottom plan view of the cover as seen along the line 3—3 of FIG. 1.

FIG. 4 is a staggered top plan and transverse sectional view of the container taken along the line 4—4 of FIG. 1.

FIG. 5 is an enlarged axial sectional view taken through the cover with the piston in its elevated or bleed position, some parts appearing in elevation.

FIG. 6 is a plan view of the operating knob, showing the face of the pressure gage.

DESCRIPTION OF PREFERRED EMBODIMENT

There is an open-top, cup-shaped, generally cylindrical container 10 cast of form-retaining, transparent plastic material or synthetic resin (such as the earlier mentioned "Lexan"), the side wall 12 being formed of successively inset or stepped, annular bands or segments 13, 14, 15, 16, which internally by their projecting edges provide support ledges 17, 18 for disk-shaped shelves 19, 20, transversely apertured at 23 with finger holes for easy removal. Externally, the encircling side wall 12 is cast integral with a plurality (here eight in number) of mutually parallel, radially outward extending, vertical ribs 22 extending downward nearly to a concave bottom wall 24 from the uppermost, mouth-encircling segment 13, and having a maximum dimension (diametric to the container 10) equal to that of the mouth segment 13. The inner face of the uppermost segment 13 is helically grooved at 26 to engage the corresponding track or threads 28 of a cover 30 when a peripheral abutment shoulder 29 comes to rest adjacent the top edge of segment 13. A lateral groove of a bottom plug segment 27 of the cover carries a sealing gasket or O-ring 31 which seats against an inner surface 11 of the container which is slanted 15°.

The cover is formed with six arcuately spaced-apart, radially directed, reinforcing ribs 36, 37, 38, 39, 40, 41 (FIG. 2) projecting from the upper face 43 and extending outward, spoke-like from the base of a centrally upstanding or axial turret 44. The turret is formed with an upward extending core 42 having an internally threaded, open-top bore 46 which distally opens into a piston chamber 48 having an open bottom 45 which by the cover being mounted atop the container is thus projected into any body of liquid which may fill the interior 21 of the container so that the liquid then rises into and fills the piston chamber to overflowing through the bleed lines. When assembled, the generally cylindrical container 10, cover 30, turret 44, threaded bore 46 and piston chamber 48 are all coaxially located. Typically the container may have a diameter on the order of six inches.

Rotatably disposed within the threaded bore 46 is an externally threaded, tubular shaft 50 which is distally connected to a piston 52. The latter has an intermediate gasket seal or O-ring 53 which thus sealingly engages or wipes the chamber wall 48 as the piston is moved up or down therein by manual manipulation of the shaft or piston stem 50. The tubular stem 50 has its interior formed with an axially cylindrical mouth section 32, followed by a frustro-conic section 33 which opens into a lower cylindrical, threaded section 34. The latter receives the threaded portion 51 of a coupling bolt 35 which has an intermediate plug portion 49 traversing the piston 52 and sealed by an O-ring 54. The flanged head 47 of the bolt is thus disposed in the piston chamber 48 and the latter is in fluid communication with the tubular interior (35, 32) of the stem 50 by a lengthwise aperture 55. The body of the piston 52 may be formed with a circle of open-bottom cavities 56 (FIGS. 3 & 5) in order to reduce the weight thereof.

The proximate or upper end of the piston stem 50 is formed with a hexagonal periphery 73 upon which is press fit an open top, peripherally ribbed knob or cup 74 which can then hold a pressure gage 75 having a threaded attachment stem 76 which is screwed into the cylindrical mouth 32 of the tubular stem 50. The gage is thus in open communication with the interior 21 of the container so as to measure the fluid pressure therein, whether gas or liquid.

The upper annular portion of the piston chamber 48 is peripherally enlarged at 58 (FIG. 5) from below the uppermost retraction or rest position of the O-ring 53 and this space is open to the exterior by four bleed lines 59, 60, 61, 62 (FIG. 2). Axial displacement of the piston downward from this position (as viewed in FIG. 5) seals the contained fluid from the exterior and subjects it to the pressure exerted by the piston as increased by turning the piston stem 50. The seating of the polygonal or square faced threads of the piston stem 50 in the correspondingly shaped grooves or track 46 of the turret core 42 enables the stem to hold or anchor at whatever rest position it is brought to, that is, to maintain the pressure built up in the chamber 21. A unit pressure effected by the exposed face or area of the piston is thus exerted on all like areas of the interior of the vessel and on such objects immersed in its fluid for the purpose of receiving such pressure.

The top face 43 of the cover 30 is recessed or dished between successive spoke-ribs 36-41 so as to form an annular series of catch basins 63, 64, 65, 66 (FIG. 2) each located adjacent a bleed line 59-62. The other two depressions 67, 68 of the series are each formed with a central boss 69, 70 which is traversed respectively by a "Schrader" TM air inlet valve 71 and a pressure relief valve 72. The latter typically may be set for 25 or 30 PSI.

We claim:
1. A pressure vessel adapted to hold gas and/or liquid and consisting of a closed-bottom, open-top container including upstanding side walls supporting an encircling top band having inner and outer faces dependent from an upper edge surrounding a wide mouth, one of the faces of said band having means for sealing engagement with the lip of a cover, the open mouth providing entry for a body of liquid adapted to fill the container to the top of said band and for removal and insertion of objects for immersed exposure to fluid pressure built up therein, a cover formed with a recessed top and a downward extending lip having inner and outer faces, one face of which has complementary means for sealing engagement with the engagement means of said band, the cover being formed with a downwardly projecting piston chamber having a proximate closed end and a distal open end, which distal end is insertable into said body of liquid so as to approximately fill the piston chamber with liquid when the cover is mounted on said container full of liquid, a piston disposed within said chamber, carried by a manually operable piston stem projecting outward through said closed end and cover, the closed end of the piston chamber having vent means adapted, when the piston is retracted against said closed end, to vent excess liquid forced from the container by mounting of the cover on the liquid-filled container, the recessed top of the cover forming a catch basin for receiving and holding such vented liquid, said vent means being closed by downward extension of the piston in exerting pressure of the body of thus-enclosed fluid, said pressure vessel additionally containing pressure relief valve means and gas inlet valve means whereby the enclosed space provided jointly by the container and mounted cover may be selectively occupied in whole or part by compressed gas introduced through said valve means.

2. A pressure vessel according to claim 1 wherein the outer end of said piston stem forms an operating knob and carries a pressure gage operatively disposed in fluid communication with the body of enclosed fluid by conduit means longitudinally traversing the piston stem and piston.

3. A pressure vessel according to claim 1 wherein said container is formed of transparent resin and the encircling side walls of the container are shaped as successively downward instepped, integral, annular segments dependent from a segment of maximum periphery surrounding the mouth, inner terminal edges of successive inset segments providing support ledges for individual, removable shelves of correspondingly decreased periphery respectively disposed thereupon, said vertically directed reinforcing ribs of the encircling side walls extending radially outward from successive annular segments so as to locate an outermost vertical edge in alignment with the periphery of the mouth-surrounding segment, said cover including a generally cylindrical, axially screwthreaded turret upstanding from an upper face thereof and threadedly traversed by said piston stem, the upper face of said body being formed with spoke-like reinforcing ribs transversely extending radially outward from the sides of the turret.

4. A pressure vessel according to claim 3 wherein said transparent resin in polycarbonate resin and said vessel is capable of retaining a fluid pressure of up to about 30 PSI.

5. A pressure vessel according to claim 2 wherein said piston stem is tubular and the piston is coupled thereto by an axially extending bolt which is longitudinally apertured and comprises said conduit means whereby the body fluid retained in the sealed container remains in fluid communication with the pressure gage.

* * * * *